US005616130A

United States Patent [19]
Mayer

[11] Patent Number: 5,616,130
[45] Date of Patent: Apr. 1, 1997

[54] NEEDLELESS INJECTION SITE

[75] Inventor: Bruno Franz P. Mayer, Santa Ana, Calif.

[73] Assignee: Nima Enterprises, Inc., Brea, Calif.

[21] Appl. No.: 493,744

[22] Filed: Jun. 22, 1995

Related U.S. Application Data

[63] Continuation-in-part of Ser. No. 401,854, Mar. 10, 1995, which is a continuation-in-part of Ser. No. 262,994, Jun. 20, 1994, Pat. No. 5,470,319.

[51] Int. Cl.$^6$ .......................... A61M 5/178; A61M 5/00; A61M 25/00
[52] U.S. Cl. .................... 604/167; 604/264; 604/256; 604/283
[58] Field of Search ................................. 604/245, 246, 604/256, 283, 414, 905, 167; 128/214

[56] References Cited

U.S. PATENT DOCUMENTS

| | | | |
|---|---|---|---|
| 4,655,752 | 4/1987 | Houkanen et al. | 604/167 |
| 4,874,377 | 10/1989 | Newgard et al. | 604/167 |
| 5,064,416 | 11/1991 | Newgard et al. | 604/167 |
| 5,154,703 | 10/1992 | Bonaldo | 604/244 |
| 5,207,661 | 5/1993 | Repschlager | 604/317 |
| 5,242,425 | 9/1993 | White et al. | 604/283 |
| 5,250,033 | 10/1993 | Evans et al. | 604/167 |
| 5,273,533 | 12/1993 | Bonaldo | 604/83 |
| 5,336,192 | 8/1994 | Palestrant | 604/167 |

FOREIGN PATENT DOCUMENTS

| | | |
|---|---|---|
| 2001732 | 4/1990 | Canada. |
| 0544581 | 11/1992 | France. |
| 3105437 | 10/1982 | Germany. |

OTHER PUBLICATIONS

"Universal Connector with Valve" –Stat—Link–Safe Tech Medical Products, Inc. –2–Page Brochure.

*Primary Examiner*—David Isabella
*Assistant Examiner*—David J. Cho
*Attorney, Agent, or Firm*—Stetina Brunda & Buyan

[57] ABSTRACT

A needleless injection site comprising a housing which defines an interior chamber and a central opening which communicates with the interior chamber. The housing further defines a proximally extending dilator projection portion which is co-axially aligned with the central opening and a distally extending adapter portion. The dilator projection and adapter portions define a continuous fluid passage. Disposed within the central opening and the interior chamber is a reseal member which has an elastically openable and closable aperture formed therein. The reseal member normally resides in a first position within the housing wherein the aperture is in a closed configuration. The reseal member is deformable such that the application of distally directed pressure thereto will cause the reseal member to distally advance within the housing to a second position wherein the aperture assumes an open configuration and communicates with the fluid passage. The cessation of the application of distally directed pressure to the reseal member will cause it to resiliently return to the first position wherein the aperture reassumes the closed configuration.

29 Claims, 2 Drawing Sheets

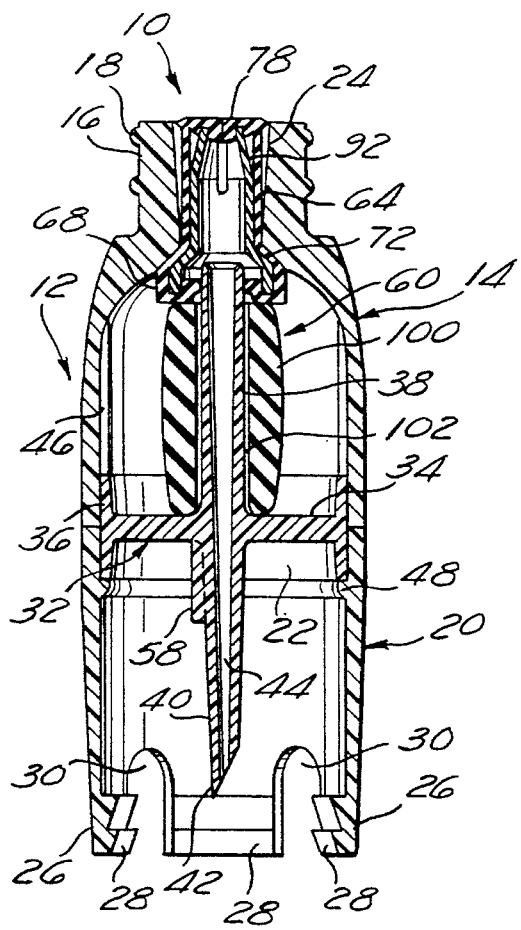
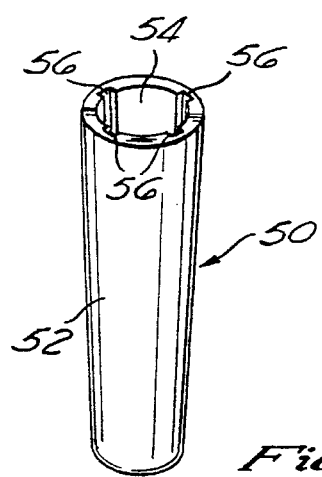
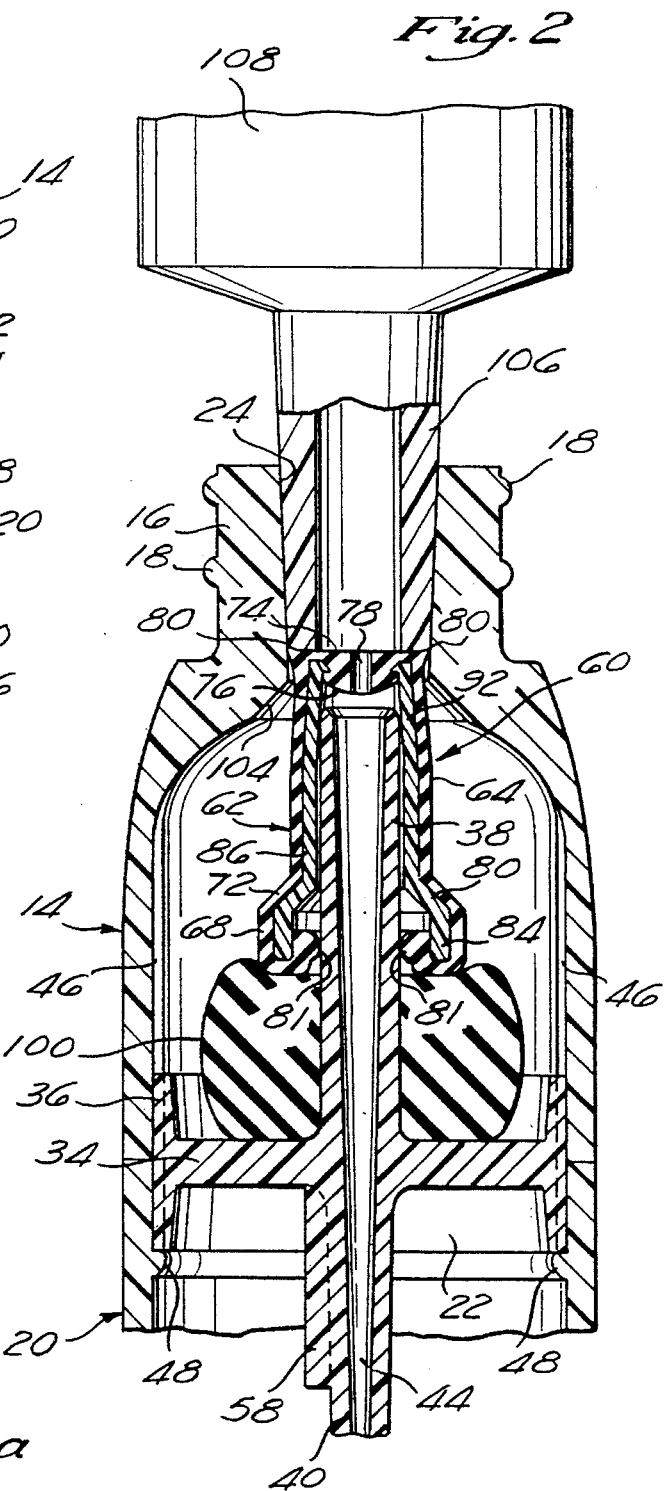
Fig. 1
Fig. 1a
Fig. 2

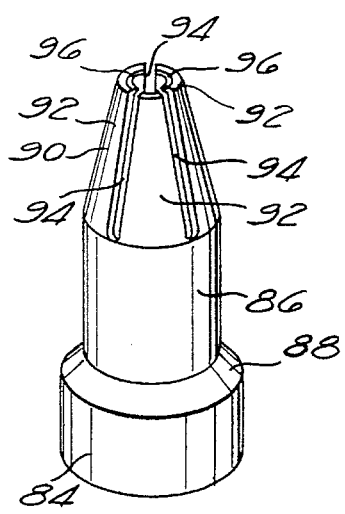
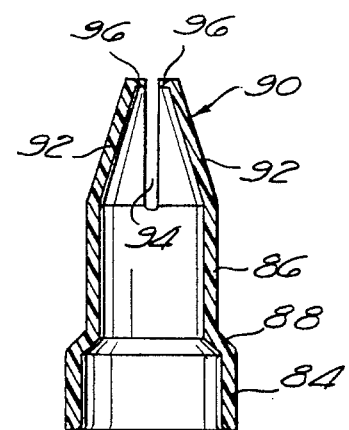
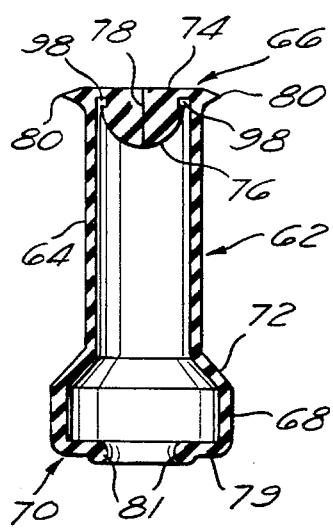
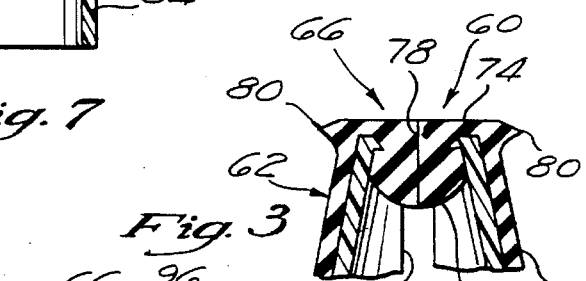
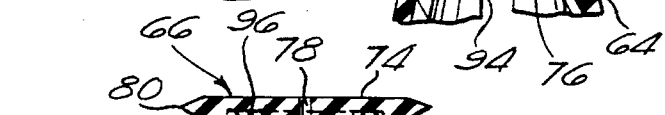
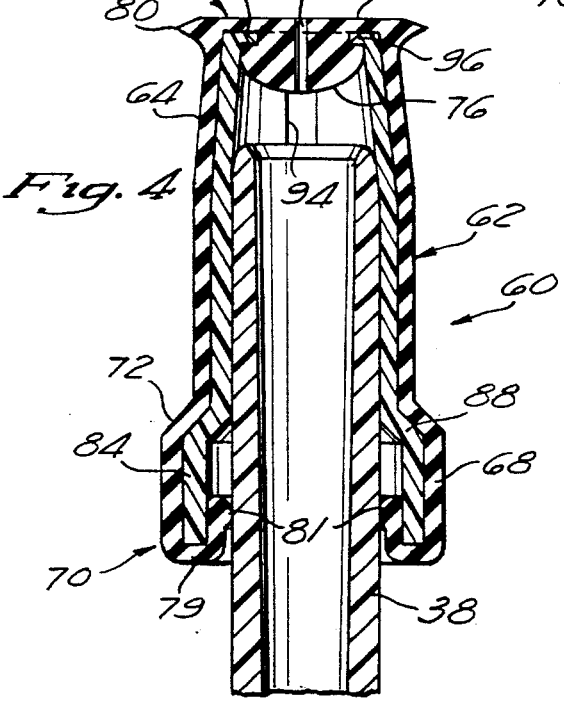

NEEDLELESS INJECTION SITE

FIELD OF THE INVENTION

The present application is a continuation-in-part of U.S. application Ser. No. 08/401,854 entitled NEEDLELESS INJECTION SITE filed Mar. 10, 1995, which is a continuation-in-part of U.S. application Ser. No. 08/262,994 entitled NEEDLELESS INJECTION SITE filed Jun. 20, 1994, now U.S. Pat. No. 5,470,319, the disclosures of which are expressly incorporated herein by reference. The present invention relates generally to the medical arts, and more particularly to a needleless injection site for use in relation to intravenous infusions.

BACKGROUND OF THE INVENTION

It is common medical practice to intravenously infuse various fluids into the blood vessels of a patient. Such infusion is typically accomplished by the insertion of a hollow introducer needle into a target blood vessel. The introducer needle is fluidly connected to one end of an elongate, flexible tube, the opposite end of which is fluidly connected to a solution bag. The solution bag itself is typically suspended above the patient so as to allow the fluid to flow downwardly through the tubing and into the patient's blood vessel via the introducer needle which remains operatively positioned therewithin. The fluid tube and solution bag are connected to each other via a metering apparatus which controls the infusion rate of fluid from the bag into the tube.

In many intravenous infusion assemblies, an injection site is fluidly coupled within the tubing intermediate the introducer needle and the solution bag. The injection site typically has a Y-shaped configuration and comprises a tubular main body portion having a tubular side arm portion in fluid communication therewith. The distal end of the side arm portion is fluidly connected to the solution bag via an upper segment of the tubing, with the bottom end of the main body portion being fluidly connected to the introducer needle via a lower segment of the tubing. The top end of the main body portion is itself covered by a diaphragm which is typically fabricated from rubber or a similar resilient material.

The inclusion of the injection site within the tubing allows various medications to be selectively infused into the blood vessel of the patient by the addition thereof to the solution flowing from the solution bag into the blood vessel via the upper tubing segment, injection site, lower tubing segment and introducer needle. This supplemental infusion is typically accomplished through the utilization of a conventional syringe, the needle of which pierces and is extended through the diaphragm disposed on the top end of the main body portion of the injection site. Subsequent to the expulsion of the medication from within the syringe and into the flowing solution, the needle is retracted out of the main body portion of the injection site, with the aperture created in the diaphragm due to the passage of the needle therethrough being substantially closed upon such retraction due to the resiliency of the diaphragm. As will be recognized, the incorporation of the injection site within the tubing allows various medications to be intravenously administered to the patient through the existing infusion site within the blood vessel, thus eliminating the need to subject the patient to additional needle sticks.

Though providing certain benefits to the patient, the injection sites constructed in accordance with the prior art possess certain deficiencies which detract from their overall utility. As previously explained, the use of such injection sites typically requires that the needle of the conventional syringe be extended through (i.e., puncture) the diaphragm attached to the top end of the main body portion of the injection site. However, the necessity of having to utilize a syringe with a needle to facilitate the introduction of the medication into the solution flow is undesirable due to the risk of inadvertent needle sticks. In recognition of this deficiency, there has also been developed in the prior art needleless injection sites which incorporate a diaphragm adapted to assume open and closed configurations without having a needle inserted thereinto. Through these needleless injection sites eliminate the need of having to puncture the diaphragm with a needle, they also possess certain deficiencies which detract from their overall utility. Foremost of these deficiencies is the difficulty associated with disinfecting the injection site, and in particular the diaphragm thereof, subsequent to medication being infused thereinto. In this respect, after each use of the injection site the diaphragm must be cleaned, with such cleaning typically being accomplished through the application of alcohol or a similar disinfecting substance thereto. However, due to the configuration of the diaphragm, complete and effective disinfection thereof is often difficult to achieve, thus increasing the risk of the introduction of contaminates into the solution stream upon subsequent uses of the injection site.

In an effort to overcome the deficiencies associated with the prior art injection sites, Applicant developed the needleless injection sites disclosed in the previously identified co-pending applications which are the parents of the present application. The present needleless injection site constitutes an improvement over that disclosed in Ser. No. 08/262,994 in that the same is adapted to accommodate needled introducers as well as non-needled introducers in the event the infusion of medication into the injection site must be accomplished in a short time during an emergency situation through the use of a needled introducer.

SUMMARY OF THE INVENTION

In accordance with the present invention, there is provided a needleless injection site comprising a housing which defines an interior chamber and a central opening which communicates with the interior chamber. Preferably formed on the outer surface of the housing about the central opening thereof are Luer threads. The housing further defines an elongate, proximally extending dilator projection portion which is co-axially aligned with the central opening, and an elongate, distally extending adapter portion. The dilator projection and adapter portions define a continuous fluid passage.

The needleless injection site further comprises a reseal member which is disposed within the central opening and the interior chamber of the housing. The reseal member includes an elastically openable and closable aperture formed therein, and normally resides in a first position within the housing wherein the aperture is in a closed configuration. The dilator projection portion of the housing extends into the reseal member. In the preferred embodiment, the reseal member is deformable such that the application of distally directed pressure thereto will cause the reseal member to distally advance within the housing to a second position wherein the aperture assumes an open configuration and communicates with the fluid passage. The removal of the distally directed pressure from the reseal member causes it to resiliently return to the first position wherein the aperture reassumes the closed configuration.

The reseal member comprises a resilient body defining a distal end, a proximal end having inner and outer surfaces, and an aperture extending between the inner and outer surfaces of the proximal end. Disposed within the body is a radial leaf spring which defines a plurality of leaf portions. The leaf portions are adapted to apply a radially inward biasing force to the proximal end of the body which maintains the aperture in the closed configuration when no distally directed pressure is applied to the outer surface of the proximal end. The reseal member further comprises an elongate, cylindrically shaped doughnut spring having a first end which is abutted against the distal end of the body, a second end, and a bore extending longitudinally therethrough. Both the body and doughnut spring of the reseal member are preferably fabricated from silicone.

The dilator projection portion of the housing is extended through the bore of the doughnut spring and into the radial leaf spring. The application of distally directed pressure to the outer surface of the proximal end of the body causes the radial leaf spring to be distally advanced over the dilator projection portion. The resultant outward flexion of the leaf portions facilitates the radial expansion of the aperture to the open configuration. Conversely, the removal of the distally directed pressure from the outer surface causes the radial leaf spring to be proximally withdrawn from over the dilator projection portion, thus facilitating the return of the aperture to the closed configuration. The body portion of the reseal member preferably comprises a generally cylindrical proximal portion defining the proximal end and a generally cylindrical distal portion defining the distal end. Formed between the proximal and distal portions is a beveled shoulder. The diameter of the distal portion preferably exceeds the diameter of the proximal portion.

In the preferred embodiment, the body of the reseal member includes a lip which is formed about and extends radially outward from the proximal end thereof, and has a diameter which slightly exceeds the diameter of the central opening of the housing. The inner surface of the proximal end has a generally semi-spherical configuration, with the aperture extending axially between the outer surface of the proximal end and the apex of its semi-spherical inner surface. The inner surface of the proximal end may further include a duck-bill style check valve formed at the apex thereof, with the aperture extending through the check valve. When the dilator projection portion is extended through the bore and into the radial leaf spring of the reseal member, both the shoulder of the body and the second end of the doughnut spring are abutted against the housing, with a slight compression force being applied to the doughnut spring. The body further defines an annular flange which extends radially inward from the distal end thereof and is abutted against the dilator projection portion when the same is extended through the bore.

In the needleless injection site, the adapter portion of the housing preferably comprises an elongate spike having a tapered outer surface and a beveled distal tip. Slidably extensible and frictionally maintainable on the spike is a tubular adapter sleeve which has a tapered outer surface and a tapered bore extending longitudinally therethrough. The tapered bore is complimentary to the outer surface of the spike for facilitating the frictional retention of the adapter sleeve thereon. The spike further includes an elongate rib formed on the outer surface thereof, with the bore of the adapter sleeve defining at least one elongate slot therewithin which is sized and configured to receive the rib when the adapter member is slidably advanced over the spike. The receipt of the rib into the slot is operable to prevent the rotation of the adapter sleeve upon the spike.

In the needleless injection site, the housing itself also includes a distal lock region for facilitating the connection of the housing to an annular surface. The lock region defines a plurality of Luer thread pitch barbs therewithin. Rather than comprising a spike, the adapter portion of the housing may alternatively define a tapered outer surface with a blunt distal tip, with the distal lock region of the housing circumventing the adapter portion and comprising an internally threaded lock member which is rotatably connected to the adapter portion.

The housing preferably comprises an upper section defining the central opening and a lower section attached to the upper section, with the upper and lower sections defining the interior chamber when attached to each other. In addition to the upper and lower sections, the housing comprises an adapter member which includes a flange portion having the dilator projection portion extending proximally from one side thereof and the adapter portion extending distally from the other side thereof. The flange portion of the adapter member is captured between the upper and lower sections of the housing, with at least a portion of the adapter member residing within the interior chamber of the housing. The adapter portion preferably has a tapered outer surface and a beveled distal tip, with the lower section of the housing defining a distal lock region for facilitating the connection of the housing to an annular surface.

BRIEF DESCRIPTION OF THE DRAWINGS

These, as well as other features of the present invention, will become more apparent upon reference to the drawings wherein:

FIG. 1 is a cross-sectional view of a needleless injection site constructed in accordance with the present invention, illustrating the reseal member thereof in a first, closed position;

FIG. 1a is a top perspective view of an adapter sleeve which may be used with the needleless injection site shown in FIG. 1;

FIG. 2 is a partial cross-sectional view of the needleless injection site shown in FIG. 1, illustrating the reseal member thereof as deformed into a second, open position;

FIG. 3 is a cross-sectional view of the proximal portion of the reseal member of the needleless injection site while in the first, closed position;

FIG. 4 is a cross-sectional view of the proximal portion of the reseal member of the needleless injection site while in the second, open position;

FIG. 5 is a cross-sectional view of the body of the reseal member;

FIG. 6 is a top perspective view of the radial leaf spring of the reseal member;

FIG. 7 is a cross-sectional view of the radial leaf spring shown in FIG. 6; and

FIG. 8 is a cross-sectional view of the proximal portion of a reseal member constructed in accordance with a second embodiment of the present invention.

DETAILED DESCRIPTION OF THE PREFERRED EMBODIMENT

Referring now to the drawings wherein the showings are for purposes of illustrating a preferred embodiment of the present invention only, and not for purposes of limiting the same, FIG. 1 illustrates a needleless injection site 10 constructed in accordance with the present invention. As seen in FIGS. 1 and 2, the injection site 10 comprises a hollow housing 12. The housing 12 itself comprises an upper section 14 which defines a reduced diameter proximal portion 16 having Luer threads 18 formed on the outer surface thereof. In addition to the upper section 14, the housing 12 comprises a sleeve-like lower section 20 which is attachable to the upper section 14. The upper and lower sections 14, 20 when attached to each other, define an interior chamber 22 of the housing 12, with the proximal half of the interior chamber 22 being defined by the upper section 14, and the distal half of the interior chamber 22 being defined by the lower section 20.

The proximal portion 16 of the upper section 14 defines a tapered central opening 24 which communicates with the interior chamber 22, and in particular the proximal half thereof. Disposed about the distal rim of the lower section 20 in equidistantly spaced intervals are a plurality of locking tabs 26, each of which includes Luer thread pitch barbs 28 formed on the inner surface thereof. The locking tabs 26 are separated from each other by arcuate cut-outs 30. Importantly, the cut-outs allow the locking tabs 26 and associated pitch barbs 28 to be flexed outwardly, for reasons which will be discussed in more detail below.

In addition to the upper and lower sections 14, 20, the housing 12 comprises an adapter member 32 which includes a central, circularly configured flange portion 34. Formed about the peripheral edge of the flange portion 34 is a perpendicularly extending wall portion 36. Extending proximally from the flange portion 36 is an elongate dilator projection portion 38 which is co-axially aligned with the central opening 24 of the upper section 14. Extending distally from the flange portion 34 is an elongate adapter portion 40 which is itself co-axially aligned with the dilator projection portion 38. The adapter portion 40 has a tapered outer surface and includes a beveled distal end which defines a piercing tip 42. The dilator projection and adapter portions 38, 40 define a continuous fluid passage 44. In the preferred embodiment, the adapter member 32 is attached to the remainder of the housing 12 via the rigid capture of the wall portion 36 thereof between the upper and lower sections 14, 20, and in particular a first shoulder 46 formed about the inner surface of the upper section 14 and an annular second shoulder 48 formed about the inner surface of the lower section 20.

Referring now to FIGS. 1 and 1a, the housing 12 may further comprise a tubular adapter sleeve 50 which is selectively attachable to the adapter portion 40 of the adapter member 32. The adapter sleeve 50 has a tapered outer surface 52 and includes a tapered bore 54 extending longitudinally therethrough which is complimentary to the tapered outer surface of the adapter portion 40. Disposed within the side wall of the bore 54 are a plurality of equidistantly spaced slots 56 which extend longitudinally from the end of the adapter sleeve 50 of greater diameter to a depth which is approximately ¼ of the total length of the adapter sleeve 50. In attaching the adapter sleeve 50 to the remainder of the housing 12, the same is slidably advanced over the adapter portion 40. Since the outer surface of the adapter portion 40 and the bore 54 of the adapter sleeve 50 have mutually tapered configurations, the adapter sleeve 50 is frictionally maintained on the adapter portion 40 subsequent to being slidably advanced thereover.

Each of the slots 56 of the adapter sleeve 50 is sized and configured to slidably receive an elongate rib 58 which is formed on the outer surface of the adapter portion 40 and extends longitudinally from the flange portion 34 along approximately ⅓ of the length of the adapter portion 40. The advancement of the adapter sleeve 50 over the adapter portion 40 is terminated when the rib 58 is fully received into a respective slot 56. Advantageously, the receipt of the rib 48 into a respective slot 56 prevents any rotation of the adapter sleeve 50 upon the adapter portion 40. Unlike the distal end of the adapter portion 40, the end of the adapter sleeve 50 opposite that including the slots 56 has a blunt configuration. The use of the adapter sleeve 50 will be discussed in more detail below.

Referring now to FIGS. 1–5, the injection site 10 constructed in accordance with the present invention further comprises a reseal member 60 which is disposed within the central opening 24 and interior chamber 22 of the housing 12. As best seen in FIGS. 4 and 5, the reseal member 60 comprises a resilient body 62 having a generally cylindrical proximal portion 64 which defines a proximal end 66, and a generally cylindrical distal portion 68 which defines a distal end 70. Formed between the proximal and distal portions 64, 68 is a beveled shoulder 72. The diameter of the distal portion 68 exceeds the diameter of the proximal portion 64. The proximal portion 64 resides within the central opening 24, with the distal portion 68 and shoulder 72 residing within the interior chamber 22. The proximal end 66 of the body 62 preferably defines a generally flat outer surface 74 and a generally semi-spherical inner surface 76. Extending axially through the proximal end 66 from the outer surface 74 to the apex of the inner surface 76 is an aperture 78. Additionally, formed about and extending radially outward from the proximal end 66 is a continuous lip 80 having a diameter which slightly exceeds the diameter of the central opening 24. Moreover, formed about and extending radially inward from the distal end 70 is a continuous annular flange 79, the inner peripheral edge of which defines an enlarged bead 81 having a generally circular sectional configuration. The body 62 is preferably fabricated from silicone, though the same may alternatively be fabricated from a similar resilient material such as rubber.

Referring now to FIGS. 3–7, the reseal member 60 further comprises a radial leaf spring 82 which is disposed within the body 62. The radial leaf spring 82 comprises a generally cylindrical base portion 84 and a generally cylindrical central portion 86 which are separated by a beveled shoulder 88. The central portion 86 transitions into a frusto-conical portion 90 which itself comprises three (3) identically configured, equidistantly spaced leaf portions 92. The leaf portions 92 are separated from each other by three (3) longitudinally extending slots 94 which extend to the central portion 86. Formed on the inner surfaces of the ends of respective ones of the leaf portions 92 are locking projections 96.

In the preferred embodiment, the radial leaf spring 82 is disposed within the body 62 in a manner wherein the proximal portion 64 extends along the outer surface of and covers the central portion 86, with the beveled shoulder 72 extending along the outer surface of and covering the beveled shoulder 88. Additionally, the distal portion 68 of the body 62 extends along the outer surface of and covers the base portion 84 of the radial leaf spring 82, with the annular flange 79 extending over and covering the rim 85 of the base portion 84. As best seen in FIGS. 3 and 4, the inner surface 76 of the proximal end 66 also bulges inwardly into the opening defined by the ends of the leaf portions 92, with the locking projections 96 of the leaf portions 92 being received into a continuous channel 98 formed within and extending about the inner surface 76. The radial leaf spring 82 is preferably fabricated from polysulfone or polycarbonate, though similar rigid materials with memory may be utilized as an alternative.

As best seen in FIGS. 1 and 2, the reseal member 60 also comprises an elongate, cylindrically shaped axial doughnut spring 100 which includes a bore 102 extending longitudinally (i.e., axially) therethrough. As will be discussed in more detail below, the doughnut spring 100 defines a first or proximal end which is normally abutted against the distal end 70 of the body 62, and a second or distal end which is normally abutted against the housing 16, and in particular the flange portion 34 of the adapter member 32. Like the body 62, the doughnut spring 100 is also preferably fabricated from silicone, though the same may alternatively be fabricated from a similar resilient material such as rubber.

In the reseal member 60, the aperture 78 extending through the proximal end 66 is elastically openable and closable. The reseal member 60 normally resides in a first position within the housing 12 (shown in FIG. 1) wherein the aperture 78 is in a closed configuration, and is deformable such that the application of distally directed pressure thereto will cause it to distally advance within the housing 12 to a second position (shown in FIG. 2) wherein the aperture 78 assumes an open configuration and communicates with the fluid passage 44 of the adapter member 32. Due to the resiliency of the doughnut spring 100 as well as the body 62, the removal of the distally directed pressure from the reseal member 60 will cause the same to resiliently return to the first position wherein the aperture 78 reassumes the closed configuration.

When the reseal member 60 is in the first position shown in FIG. 1, the dilator projection portion 38 of the adapter member 32 is extended through the bore 102 of the doughnut spring 100 and into the hollow interior of the radial leaf spring 82, with the proximal end of the dilator projection portion 38 extending to approximately the beveled shoulder 88 of the radial leaf spring 82. When extended into the radial leaf spring 82, the dilator projection portion 38 passes through the opening defined by the annular flange 79 of the body 62, and in particular the bead 81 thereof. Importantly, the diameter of the opening defined by the bead 81 is less than the outer diameter of the dilator projection portion 38. As such, when the dilator projection portion 38 passes through this opening, the annular flange 79 is turned inwardly into the interior of the base portion 84 of the radial leaf spring 82, with the bead 81 being sealed against the outer surface of the dilator projection portion 38, as best seen in FIGS. 1, 2 and 4.

In addition to the dilator projection portion 38 being extended through the bore 102 and into the radial leaf spring 82 when the reseal member 60 is in the first position, the outer surface 74 of the proximal end 66 is substantially flush with the rim of the proximal portion 16 of the upper section 14, with the peripheral edge of the lip 80 formed about the proximal end 66 being abutted against the side wall of the central opening 24. Further, the beveled shoulder 72 of the body 62 is abutted against a complimentary beveled ramp 104 which defines the transition between the central opening 24 and interior chamber 22 of the housing 12. As previously indicated, the proximal end of the doughnut spring 100 is abutted against the distal end 70 of the body 62, and in particular the annular flange 79, with the distal end of the doughnut spring 100 being abutted against the flange portion 34 of the adapter member 32.

In the preferred embodiment, the distance separating the ramp 104 from the flange portion 34 of the adapter member 32 slightly exceeds the combined length of the distal portion 68 of the body 62 and doughnut spring 100. As such, when the reseal member 60 is disposed in the first position within the housing 12, the doughnut spring 100 is slightly compressed between the distal end 70 of the body 62 and flange portion 34, thus applying a pre-load thereto which causes the same to bulge slightly outwardly as shown in FIG. 1. Importantly, when the reseal member 60 is in the first position, the leaf portions 92 of the radial leaf spring 82 apply a radially inwardly biasing force to the proximal end 66 of the body 62 which maintains the aperture 78 in the closed configuration. As seen in FIG. 1, when the aperture 78 is in the closed configuration, a slight gap is typically defined between the outer surfaces of the leaf portions 92 and the proximal portion 64 of the body 62.

As best seen in FIGS. 2 and 4, the application of distally directed pressure to the outer surface 74 of the proximal end 66 by a device such as the tip 106 of an introducer device 108 causes the radial leaf spring 82 to be distally advanced over the dilator projection portion 38. Such advancement removes the shoulder 72 out of its abutting contact with the ramp 104 and facilitates the compression of the doughnut spring 100, thus causing the same to bulge outwardly. Importantly, the camming action of the dilator projection portion 38 against the inner surfaces of the leaf portions 92 causes the same to be flexed outwardly, thus facilitating the radial expansion of the aperture 78 to the open configuration. Due to the resiliency of the doughnut spring 100, the removal of the distally directed pressure from the outer surface 74 of the proximal end 66 causes the radial leaf spring 82 to be proximally withdrawn from over the dilator projection portion 38, thus facilitating the return of the reseal member 60 to the first position and resultant collapse of the aperture 78 to the closed configuration.

When the reseal member 60 is moved to the second position and the aperture 78 opened as shown in FIGS. 2 and 4, a continuous flow path is created between the introducer device 108 and fluid passage 44 of the adapter member 32. Importantly, medication expelled from the introducer device 108 is prevented from leaking into the interior chamber 22 of the housing 12 by the abutment of the tip 106 of the introducer device 108 against the generally flat outer surface 74 of the proximal end 66, as well as the sliding seal created by the abutment of the lip 80 against the side wall of the central opening 24. Additionally, any fluid passing through the aperture 78 which does not enter the fluid passage 44 is prevented from flowing into the interior chamber 22 by the sliding seal created by the abutment of the bead 81 against the outer surface of the dilator projection portion 38. As further seen in FIGS. 2 and 4, when the reseal member 60 is moved to the second position, the proximal portion 64 of the body 62 extends along and covers the outer surfaces of the leaf portions 92.

In the preferred embodiment, the housing 12 of the injection site 10 is configured so as to allow the same to be connectible to infusion components such as a Luer connector, a Y-injection site, a standard tubular fluid line, and a bottle. In this respect, the connection of the injection site 10 to a fluid line is typically accomplished by the slidable advancement of the adapter portion 40 into the lumen of the fluid line, with the adapter portion 40 being frictionally maintained therewithin. The coupling of the injection site 10 to the other infusion components such as the Luer connector, Y-injection site and bottle is typically accomplished through the utilization of the locking tabs 26 which may be flexed outwardly and expanded over portions of such components due to the inclusion of the cut-outs 30, with the pitch barbs 28 maintaining a positive engagement between the housing 12 and a particular component. Typically, when the injection site 10 is to be connected to a Luer connector, the adapter sleeve 50 will be attached to the adapter portion 40 in the aforementioned manner. It will be recognized that other injection sites may be fabricated which comprise the reseal member 60 incorporated into a differently configured housing without departing from the spirit and scope of the invention. In this respect, any housing with which the reseal member 60 is utilized need only be configured so that the reseal member 60 is movable from the first to the second positions to create a continuous fluid passage from the introducer device into the infusion component in the previously described manner.

Due to the configuration of the reseal member 60, in an emergency situation, medication may be passed into the fluid passage 44 via a needled introducer device rather than through the non-needled introducer device 108 previously described. In this respect, when a needled introducer device is utilized, the reseal member 60 will not be moved to the second position to facilitate the opening of the aperture 78. Rather, the needle of the needled introducer device is simply forced through the closed aperture 78 and into the fluid passage 44 of the dilator projection portion 38. Importantly, even if the tip of the needle is not extended into the fluid passage 44, medication dispensed therefrom will still flow into the fluid passage 44, and will be prevented from flowing into the interior chamber 22 by the seal created by the abutment of the bead 81 against the outer surface of the dilator projection portion 38. Advantageously, due to the locking projections 96 of the leaf portions 92 being received into the channel 98 of the inner surface 76, the plug created by the protrusion of the inner surface 76 into the opening defined by the leaf portions 92 is maintained during the removal (i.e., withdrawal) of the needle of the needled introducer device from within the aperture 78.

Referring now to FIG. 8, the reseal member 60 may alternatively be formed to include a body 62a which is substantially identical to the previously described body 62, but further includes a conically-shaped, duck-bill style check valve 110 which is formed at the apex of the semi-spherical inner surface 76a of the proximal end 66a thereof. The check valve 110 may be provided with the reseal member 60 for purposes of preventing any medication from backflowing into the introducer device 12. It will be recognized that the check valve 110 may also be formed with alternative configurations.

Additional modifications and improvement of the present invention may also be apparent to those skilled in the art. Thus, the particular combination of parts described and illustrated herein is intended to represent only certain embodiments of the present invention, and is not intended to serve as limitations of alternative devices within the spirit and scope of the invention.

What is claimed is:

1. A needleless injection site, comprising:

a housing defining:

an interior chamber;

a central opening which communicates with the interior chamber;

an elongate, proximally extending dilator projection portion; and an elongate, distally extending adapter portion, said dilator projection and adapter portions defining a continuous fluid passage;

a reseal member disposed within said central opening and said interior chamber, said reseal member comprising:

a resilient body having a distal end and a proximal end which defines inner and outer surfaces and includes an elastically openable and closable aperture extending therethrough between the inner and outer surfaces thereof;

a radial leaf spring disposed within said body and adapted to apply a radially inward biasing force to the proximal end which normally maintains the aperture in a closed configuration; and an elongate doughnut spring having a first end which is abutted against the distal end of the body, a second end, and a bore extending longitudinally therethrough, said dilator projection portion being extended through the bore of the doughnut spring and into the radial leaf spring;

said reseal member being deformable such that the application of distally directed pressure to the outer surface of the proximal end will cause the radial leaf spring to be distally advanced over the dilator projection portion which facilitates the radial expansion of the aperture to an open configuration communicating with the fluid passage, and the removal of the distally directed pressure from the outer surface will cause the radial leaf spring to be proximally withdrawn from over the dilator projection portion which facilitates the resilient return of the aperture to the closed configuration.

2. The injection site of claim 1 wherein said body comprises:

a generally cylindrical proximal portion defining said proximal end;

a generally cylindrical distal portion defining said distal end; and a beveled shoulder formed between the proximal and distal portions;

the diameter of said distal portion exceeding the diameter of said proximal portion.

3. The injection site of claim 2 wherein the second end of the doughnut spring and the beveled shoulder of the body are abutted against the housing and the doughnut spring is sized so as to be compressed between the distal end of the body and the housing when the dilator projection portion is extended through the bore into the radial leaf spring.

4. The injection site of claim 1 wherein said body includes a lip formed about and extending radially outward from the proximal end thereof, said lip having a diameter slightly exceeding the diameter of the central opening.

5. The injection site of claim 1 wherein said body includes an annular flange formed about and extending radially inward from the distal end thereof, said flange forming a seal against said dilator projection portion.

6. The injection site of claim 1 wherein said body and said doughnut spring are fabricated from silicone.

7. The injection site of claim 1 wherein the inner surface of the proximal end has a generally semi-spherical configuration and said aperture extends axially between the outer surface and the apex of the inner surface.

8. The injection site of claim 7 wherein the inner surface of the proximal end includes a check valve formed at the apex thereof, said aperture extending through said check valve.

9. The injection site of claim 8 wherein said check valve comprises a duck-bill style check valve.

10. The injection site of claim 1 wherein said radial leaf spring comprises a plurality of leaf portions, said leaf portions applying the radially biasing force to the proximal end of the body which maintains the aperture in the closed configuration.

11. The injection site of claim 1 wherein said housing defines an outer surface having Luer threads formed thereon about the central opening thereof.

12. The injection site of claim 1 wherein the adapter portion of the housing comprises a spike having a beveled distal tip.

13. The injection site of claim 12 wherein the spike has a tapered outer surface.

14. The injection site of claim 13 wherein said housing further comprises a tubular adapter sleeve slidably extensible over the spike and having a tapered bore extending longitudinally therethrough which is complimentary to the outer surface of the spike for facilitating the frictional retention of the adapter sleeve thereon.

15. The injection site of claim 14 wherein the spike includes an elongate rib formed on the outer surface thereof and the bore of the adapter sleeve defines at least one elongate slot therewithin which is sized and configured to receive the rib when the adapter member is slidably advanced over the spike, the receipt of the rib into the slot being operable to prevent the rotation of the adapter sleeve upon the spike.

16. The injection site of claim 14 wherein the adapter sleeve has a tapered outer surface.

17. The injection site of claim 1 wherein said housing further defines a distal lock region for facilitating the connection of the housing to an annular surface.

18. The injection site of claim 17 wherein said lock region defines a plurality of Luer thread pitch barbs therewithin.

19. The injection site of claim 1 wherein said housing comprises:
   an upper section defining said central opening;
   a lower section attached to said upper section, said upper and lower sections defining the interior chamber when attached to each other; and
   an adapter member comprising:
      a flange portion;
      the dilator projection portion extending proximally from the flange portion; and
      the adapter portion extending distally from the flange portion;
      said flange portion being captured between the upper and lower sections with at least a portion of the adapter member residing within the interior chamber.

20. The injection site of claim 19 wherein the reseal member is abutted against and compressed between the flange portion of the adapter member and the upper section of the housing when the dilator projection portion is extended into the reseal member.

21. The injection site of claim 19 wherein the adapter portion has a tapered outer surface and a beveled distal tip and the lower section of the housing defines a distal lock region for facilitating the connection of the housing to an annular surface.

22. A reseal member for use in a needleless injection site, comprising:
   a resilient body defining a distal end, a proximal end having inner and outer surfaces, and an aperture extending between the inner and outer surfaces of the proximal end;
   a radial leaf spring disposed within said body and defining a plurality of leaf portions, said leaf portions applying a radially inward biasing force to the proximal end of the body which maintains the aperture in a closed configuration; and
   an elongate doughnut spring which is abutted against the distal end of the body and defines a bore extending longitudinally therethrough.

23. The reseal member of claim 22 wherein the inner surface of the proximal end has a generally semi-spherical configuration, said aperture extending axially between the outer surface and the apex of the inner surface.

24. The reseal member of claim 23 wherein said leaf portions define inwardly extending locking projections and the inner surface of the proximal end includes a continuous channel formed thereabout, said locking projections being received into the channel.

25. The reseal member of claim 23 wherein the inner surface of the proximal end includes a check valve formed at the apex thereof, said aperture extending through said check valve.

26. The reseal member of claim 25 wherein said check valve comprises a duck-bill style check valve.

27. The reseal member of claim 22 wherein said body and said doughnut spring are fabricated from silicone.

28. The reseal member of claim 22 wherein said body includes an annular flange formed about and extending radially inward from the distal end thereof.

29. The reseal member of claim 22 wherein said body includes a lip formed about and extending radially outward from the proximal end thereof.

* * * * *

UNITED STATES PATENT AND TRADEMARK OFFICE
Certificate

Patent No. 5,616,130                                                                                                    Patented: April 1, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Bruno Franz P. Mayer, Santa Ana, Calif.; and Dongchul Dan Hyun, Santa Ana, Calif.

Signed and Sealed this Third Day of November, 1998.

JOHN G. WEISS
                                                                                                                 *SPE*
                                                                                                       Art Unit 3735